United States Patent [19]

Tsuboi

[11] Patent Number: 5,571,966
[45] Date of Patent: Nov. 5, 1996

[54] METHOD AND APPARATUS FOR PREDICTING LIFETIME OF MEASURED OBJECT

[75] Inventor: Kiyoshi Tsuboi, Tokyo, Japan

[73] Assignee: Iwatsu Electric Co., Ltd., Tokyo, Japan

[21] Appl. No.: 321,317

[22] Filed: Oct. 11, 1994

[30] Foreign Application Priority Data

Oct. 12, 1993 [JP] Japan .................................. 5-278972

[51] Int. Cl.$^6$ ............................ G01N 29/00; G01N 29/12
[52] U.S. Cl. ................................ 73/579; 73/630; 73/582; 73/649; 364/508
[58] Field of Search .......................... 73/579, 600, 592, 73/580, 630, 582, 573, 574, 649; 364/508

[56] References Cited

U.S. PATENT DOCUMENTS

| | | | |
|---|---|---|---|
| 3,987,665 | 10/1976 | Hansen | 73/579 |
| 4,059,988 | 11/1977 | Shaw | 73/579 |
| 4,233,849 | 11/1980 | Defebvre et al. | 73/579 |
| 4,342,229 | 8/1982 | Massa | 73/579 |
| 4,399,701 | 8/1983 | Dunlop | 73/579 |
| 4,502,329 | 3/1985 | Fukunaga et al. | 73/579 |
| 4,693,119 | 9/1987 | Johnson | 73/579 |
| 4,702,111 | 10/1987 | Holland | 73/579 |
| 4,858,469 | 8/1989 | Hosgood et al. | 73/579 |
| 5,144,838 | 9/1992 | Tsuboi | 73/579 |
| 5,408,880 | 4/1995 | Rhodes et al. | 73/579 |

Primary Examiner—Thomas P. Noland
Assistant Examiner—Helen C. Kwok
Attorney, Agent, or Firm—Finnegan, Henderson, Farabow, Garrett And Dunner, L.L.P.

[57] ABSTRACT

A nondestructive inspection method predicts the lifetime of a measured object. A measured object is made to vibrate, and there is obtained a frequency difference Δf between a frequency of a nth-order spectrum and a frequency of a (n+1)th-order spectrum of any one of longitudinal waves, transverse waves and distortional waves generated in the measured object when the measured object is made to vibrate. It is possible to predict lifetime of the measured object by detecting degree of deterioration of the measured object based on a relational curve representing the frequency difference Δf and the circumstances of use of the measured object.

7 Claims, 7 Drawing Sheets

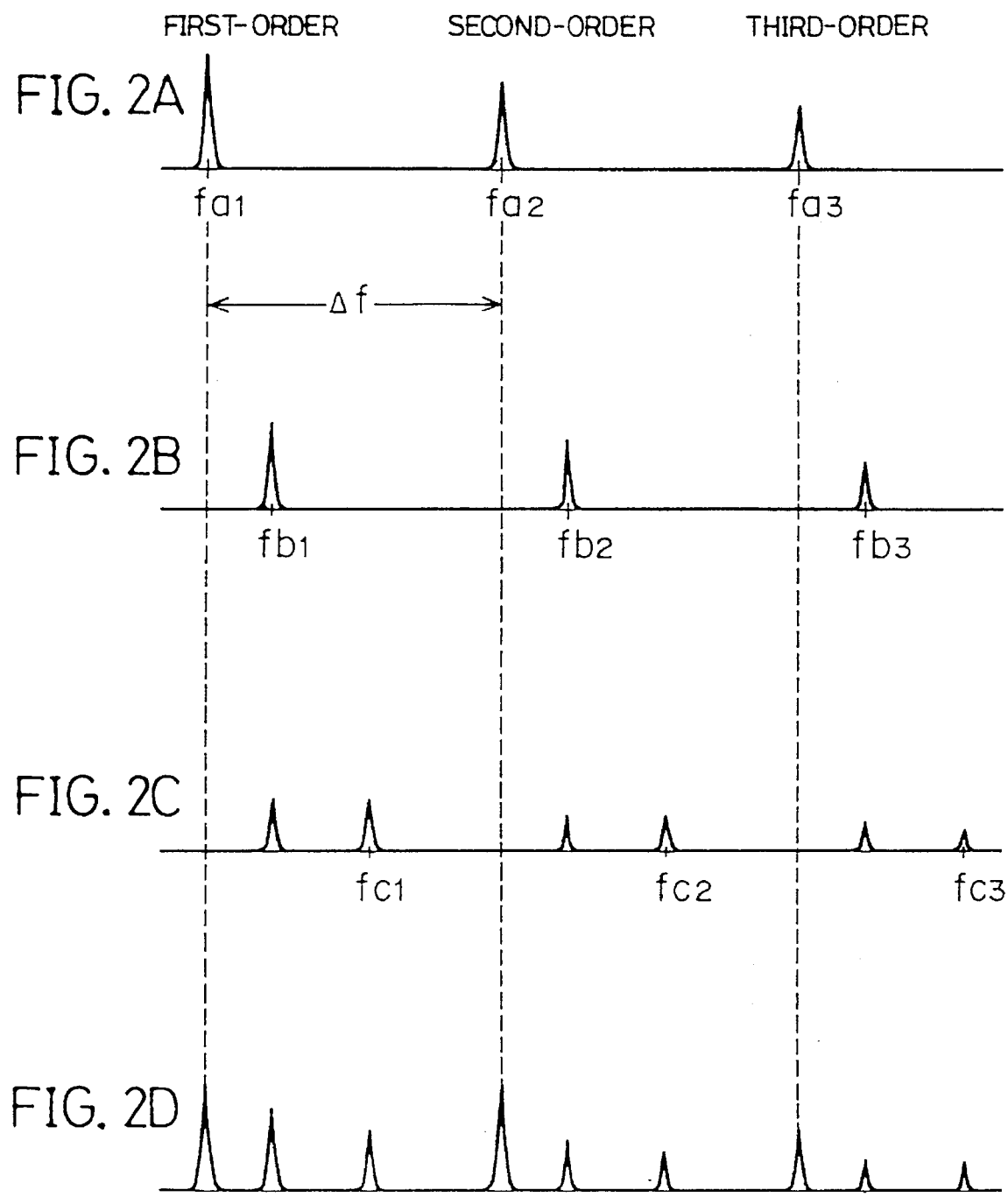

(W₁)

1

METHOD AND APPARATUS FOR PREDICTING LIFETIME OF MEASURED OBJECT

BACKGROUND OF THE INVENTION

The present invention relates to a method for predicting the lifetime of a measured object by detecting the degree of deterioration of the measured object and an apparatus therefor.

If parts of machinery or products are defective, such as when they are cracked, hollowed or concaved, such parts may break. There is then the risk that a serious accident will take place when the defective parts fail. Therefore, the existence of such defective parts preferably should be detected and the parts eliminated before any machinery or products are assembled or fabricated from them.

Heretofore, nondestructive inspection methods are known that are effective in detecting the above-mentioned defects. Nondestructive inspection methods that are now available include an ultrasonic wave reflection method of detecting defects by using ultrasonic waves reflected from defective parts or defective products, a so-called AE (acoustic emission) method for detecting defective parts or defective products based on sounds generated when defective parts or defective products are cracked, a CCD (charge-coupled device) camera inspection method for inspecting the surface of defective parts or defective products, an X-ray photograph method and a color check method.

The above-mentioned inspection methods of detecting defects or the like can detect whether or not the measured object is defective, but cannot predict how long the measured object can be used safely, i.e., the lifetime of the measured object.

Parts of machinery and products progressively deteriorate in use. In the case of turbine blades used in a turbine engine, for example, it is important to be able to predict the lifetime of the turbine blades and to exchange a defective turbine blade with a new one in a proper period before the occurrence of defects to thereby prevent a serious accident from taking place.

SUMMARY OF THE INVENTION

It is therefore an object of the present invention to provide a method and an apparatus for predicting the lifetime of a measured object in which the lifetime of the measured object can be predicted by detecting the degree of deterioration of the measured object.

According to a first aspect of the present invention, there is provided a measured object lifetime predicting method which comprises the steps of causing a measured object to vibrate, and predicting the lifetime of said measured object by detecting the degree of deterioration of the measured object based on the change of a frequency difference $\Delta f$ between a frequency of an nth-order spectrum and a frequency of a (n+1)th-order spectrum of any one of longitudinal waves, transverse waves, and distortional waves.

According to a second aspect of the present invention, there is provided a measured object lifetime predicting apparatus which comprises a vibrating apparatus for causing a measured object to vibrate, a sensing device for sensing vibrations of the measured object and converting the vibrations into an electrical signal, a spectrum analyzing device supplied with the electrical signal from the sensing device and analyzing a spectrum of stationary wave vibrations of the measured object, a frequency difference detecting device for detecting a frequency difference $\Delta f$ between a frequency of an nth-order spectrum and a frequency of a (n+1)th-order spectrum of any one of longitudinal waves, transverse waves and distortional waves, a predicting device for predicting the lifetime of the measured object by detecting the degree of deterioration of the measured object based on a relational curve representing the frequency difference $\Delta f$ and a circumstance where the measured object is in use, and an output device for outputting a result of the prediction.

In accordance with a third aspect of the present invention, there is provided a measured object lifetime predicting apparatus which comprises a vibrating device for causing a measured object to vibrate, a sensing device for picking up the vibration of the measured object and converting the vibration into an electrical signal, a spectrum analyzing device supplied with the electrical signal from the sensing device and analyzing a spectrum of a stationary wave vibration of the measured object, a frequency difference detecting device for detecting a frequency difference $\Delta f$ between a frequency of a spectrum of longitudinal waves and a frequency of a spectrum of distortional waves, a predicting device for predicting the lifetime of the measured object by detecting the degree of deterioration of the measured object based on a relational curve representing the frequency difference $\Delta f$ and a circumstance where the measured object is in use, and an output device for outputting a result of the prediction.

BRIEF DESCRIPTION OF THE DRAWINGS

FIGS. 2A through 2D are diagrams of waveforms of frequencies that explain a spectrum distribution of stationary waves generated in the measured object when the measured object is made to vibrate;

DETAILED DESCRIPTION OF THE PREFERRED EMBODIMENT

Initially, fundamental principle of the present invention will be described below prior to the description of the preferred embodiments.

Figure 1A:
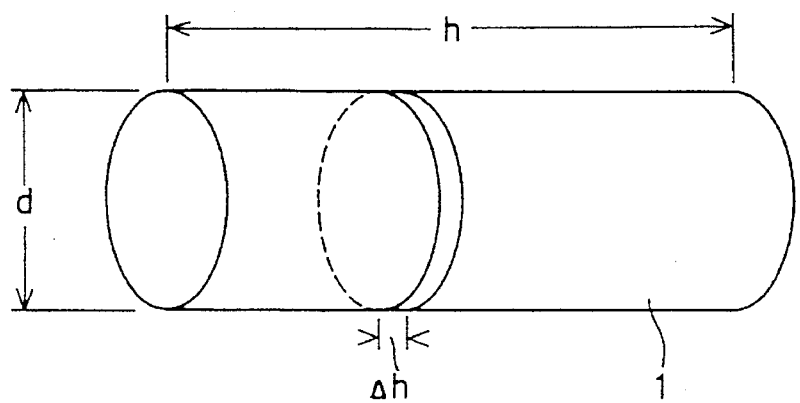
FIGS. 1A through 1D are schematic diagrams that explain stationary wave vibration generated in a measured object when the measured object is made to vibrate.

When a measured object is made to vibrate, longitudinal waves (longitudinal vibrations), transverse waves, (transverse vibrations) and distortional waves (distortional vibrations) are generated in pairs in the measured object. To facilitate the explanation, consider a cylindrical object 1 with a diameter d and a length h as shown in FIG. 1A. Assuming a very small cylinder unit 2 has a length $\Delta h$ with respect to the cylindrical object 1. When the cylindrical object 1 is made to vibrate, there are generated three kinds of oscillation waves that change the very small cylinder unit 2, as shown in FIGS. 1B, 1C and 1D.

Figure 1B:
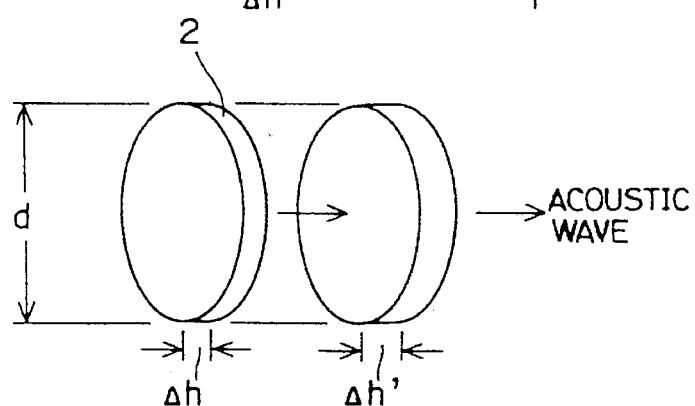
Figure 1C:
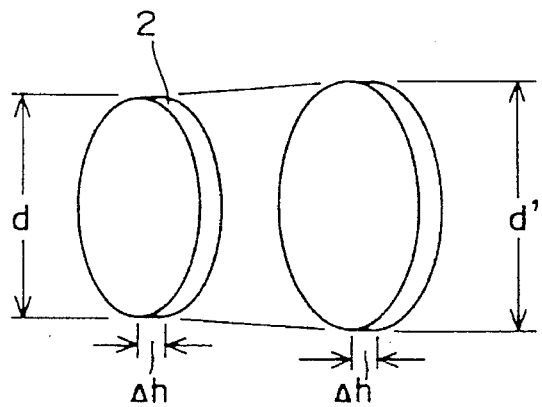
Figure 1D:
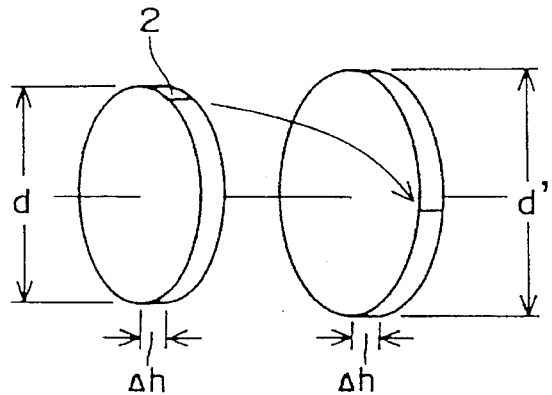

FIG. 1B is a diagram that explains longitudinal waves. The longitudinal waves are generated when the very small cylinder unit 2 vibrates such that the cylinder unit 2 changes only in the length direction as shown in FIG. 1B. The frequency of the longitudinal waves corresponds to the length between the opposite circular end faces of the cylindrical object 1. Assuming that f is the frequency and that c is the velocity of an acoustic wave, then:

$$f=cn/2h \tag{1}$$

where n is an order of harmonic wave.

FIG. 1C is a diagram that explains transverse waves. The transverse waves are generated when the very small cylinder unit 2 vibrates such that the cylinder unit 2 changes only in the direction of the diameter d while the length $\Delta h$ thereof does not change, as shown in FIG. 1C.

FIG. 1D is a diagram that explains distortional waves. The distortional waves are generated when the very small cylinder unit 2 is caused to rotate about the center line of the cylinder in a distortional rotation fashion when they propagate from one circular end face to the other circular end face of the cylindrical object 1. The distortional waves are generated together with the transverse waves when the measured object is made to vibrate.

The above-mentioned vibration waves have frequencies that are determined in accordance with the shape and size of the measured object. A measured object was made to vibrate. The vibration generated in the object was sensed by a non-contacting pickup means, and the spectrum of vibration was analyzed by a spectrum analyzer. This indicated, as shown in FIG. 2A that the longitudinal wave has a first-order spectrum observed at the position of a frequency fa1, a second-order spectrum observed at the position of a frequency fa2, and a third order spectrum at the position of frequency fa3. Similarly, as shown in FIG. 2B, it is to be noted that the transverse wave has a first-order spectrum observed at the position of a frequency fb1 (>fa1), a second-order spectrum observed at the position of a frequency fb2 (>fa2), and a third order spectrum observed at the position of frequency fb3 (>fa3). The distortional wave, as shown in FIG. 2C, has a first-order spectrum observed at the position of a frequency fc1 (>fb1 >fa1), a second-order spectrum observed at the position of a frequency fc2 (>fb2 >fa2), and a third order spectrum observed at the position of frequency fC3 (<fb3>fa3). FIG. 2D is a diagram showing a frequency spectrum distribution in which the spectra of the above-mentioned three vibration waves are observed in the mixed state.

It was ascertained that a frequency difference $\Delta fa$ between a frequency of an nth-order spectrum and a frequency of a (n+1)th-order spectrum of the respective oscillation waves corresponds to the degree of deterioration of the measured object in a one-to-one fashion; and that the frequency difference $\Delta fa$ exponentially increases as the deterioration of the measured object progresses.

Specifically, when the measured object is made to vibrate, intrinsic stationary wave vibrations are generated in the measured object so that it is possible to observe the first-order spectrum, the second order spectrum, and the third order spectrum generated at eigenfrequency positions determined by the shape and dimension of the measured object, based on the generated intrinsic stationary wave vibrations. The eigenfrequency positions, at which respective spectra are generated, are not changed so long as the degree of deterioration of the measured object is not changed.

However, as the degree of deterioration of the measured object progresses, particles, of which the substance is composed, are roughened or hardened. If the degree of deterioration of the measured object progresses in excess of a threshold level, the measured object becomes cracked or broken.

Figure 3A:
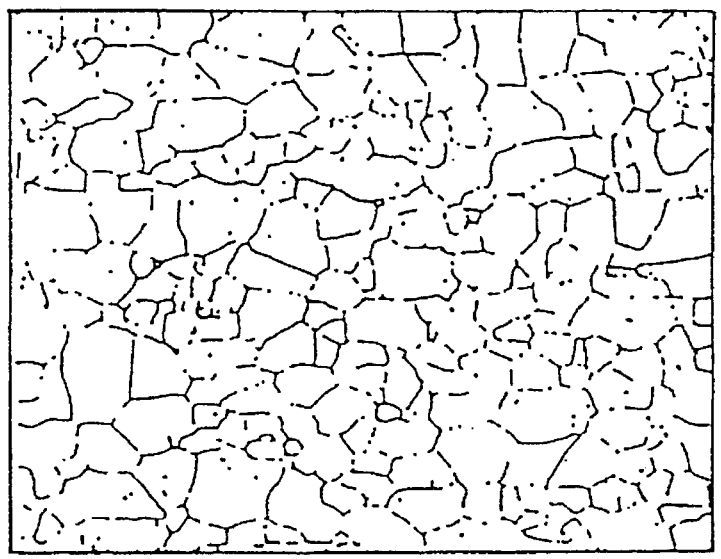
FIGS. 3A and 3B are microscopic representations that explain an example of the degree of deterioration of the measured object.
Figure 3B:
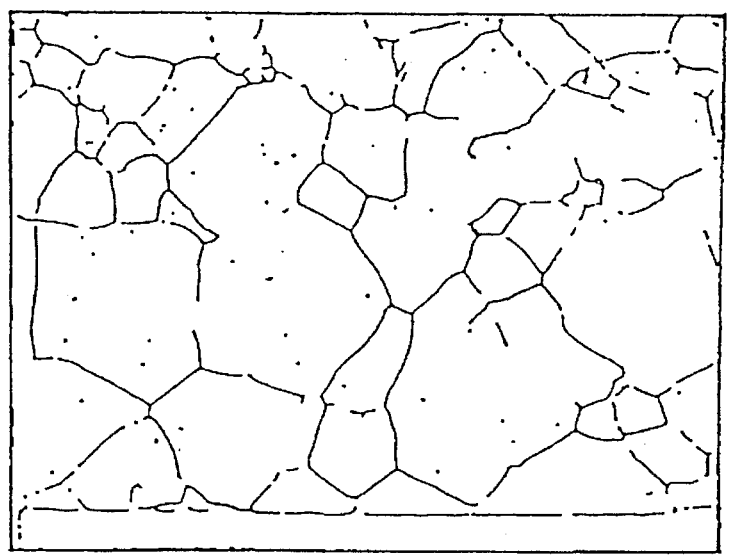

FIGS. 3A and 3B show conditions where particles of the substance are roughened as deterioration of the measured object progresses. Specifically, FIG. 3A is a microscopic representation of the granular state of a sample which is free from deterioration, i.e., a sample in satisfactory condition. FIG. 3B is a microscopic representation of the granular state of a sample whose deterioration has progressed.

Figure 4A:
FIGS. 4A and 4B are microscopic representations that explain another example of the degree of deterioration of the measured object.
Figure 4B:

FIGS. 4A and 4B show the condition where samples (casting materials) are hardened due to deterioration. Specifically, FIG. 4A is a microscopic representation of a sample which is in satisfactory condition. FIG. 4B is a microscopic representation of a sample in which graphite becomes spherically segregated after the sample is hardened due to deterioration. FIGS. 3A, 3B and FIGS. 4A, 4B are all microscopic representations showing the samples in the form of a binary image on an enlarged scale.

If the degree of roughness of the sample exceeds a threshold value, or segregation of graphite progresses, then the sample becomes defective.

When the particles are roughened or hardened, the velocity of acoustic waves which propagate in the substance increases. Oscillation waves have higher frequencies as the order of oscillation increases. Therefore, it is considered that the frequency difference $\Delta fa$ between the frequency of the nth-order spectrum and the frequency of the (n+1)th-order spectrum increases as deterioration of the measured object progresses.

Having considered a frequency difference $\Delta fb$ between frequencies of the same-order spectra of longitudinal waves and distortional waves, it is to be understood that this frequency difference $\Delta fb$ corresponds to deterioration of the measured object in a one-to-one manner, and that this frequency difference $\Delta fb$ exponentially increases as deterioration of the measured object progresses.

A measured object lifetime predicting method according to the present invention owes most of its specific features to the above-mentioned ascertainments. According to the measured object lifetime predicting method of the present invention, it is possible to predict the lifetime of the measured object by detecting deterioration of the measured object based on the change of the frequency difference $\Delta fa$ between the frequency of the nth-order spectrum and the frequency of the (n+1)th-order spectrum of any one of the longitudinal waves, the transverse waves and the distortional waves that were generated in the measured object when the measured object is made to vibrate.

Further, according to the measured object lifetime predicting method of the present invention, it is possible to predict the lifetime of the measured object by detecting deterioration of the measured object based on the change of the frequency difference $\Delta fb$ between the frequency of the spectrum of longitudinal waves and the frequency of the spectrum of distortional waves that were generated when the measured object is made to vibrate.

According to the present invention, vibration generated when the measured object is made to vibrate is analyzed by spectrum analyzer to thereby obtain the frequency difference Δfa or Δfb. From the frequency difference Δfa or Δfb thus obtained, it is possible to predict the lifetime of the measured object by checking the relationship between the previously-calculated difference Δfa or Δfb and degree of deterioration while the safety factor also is estimated.

A measured object lifetime predicting method and apparatus according to an embodiment of the present invention will now be described with reference to FIG. 5 through FIGS. 7A, 7B.

A study was made of a turbine blade composed mainly of titatium which was made to vibrate. The spectrum of oscillation of the longitudinal waves of the above-mentioned three kinds of stationary wave vibrations was then analyzed by a spectrum analyzer.

In this case, the turbine blade was made to vibrate by impacting one of the end faces perpendicular to the longitudinal direction (propagation direction of longitudinal waves) of the turbine blade. According to this vibrating method, the energy of the transverse waves and the distortion waves become very small, as compared with that of the longitudinal waves. Therefore, when the oscillation of the turbine blade is sensed and analyzed by a spectrum analyzer, it is possible to extract the spectrum of only the longitudinal waves with ease.

As earlier noted, if the length h between the opposite end faces, which are perpendicular to the longitudinal direction of the turbine blade, is known, then the aforementioned Equation (1) yields the frequency of the longitudinal waves. Then, a peak of the spectrum of the frequency of the longitudinal waves is observed at the frequency position by a spectrum analyzer.

Figure 5:
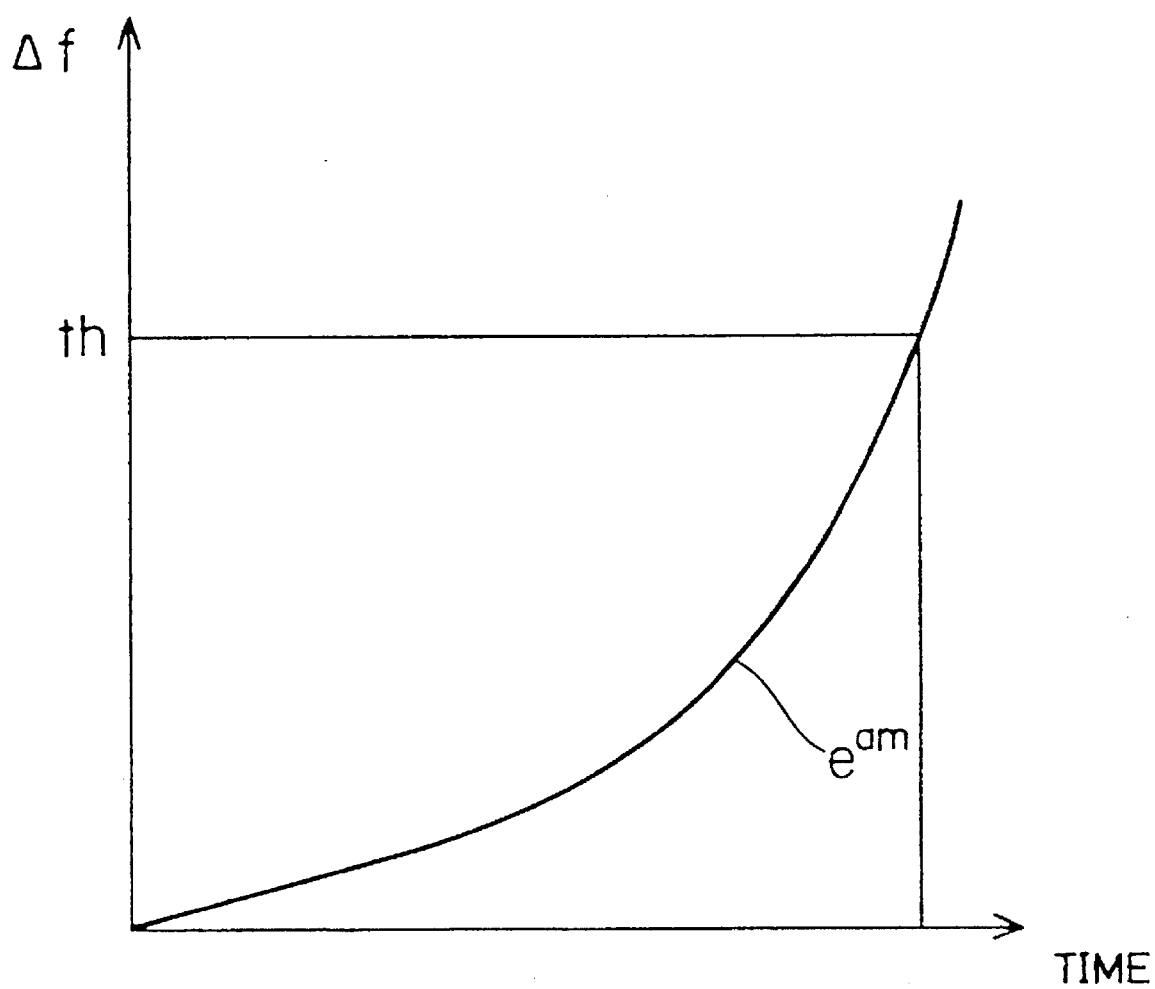
FIG. 5 is a diagram showing a characteristic curve obtained when the relationship between a frequency difference and the number of times a measured object is in use is measured.

The measured relationship between a frequency difference Δf, for example, of a frequency f1 of a first-order spectrum and a frequency f2 of a second-order spectrum and the number of times, or the time period in which the turbine blade has been in use results in the relational curve shown in FIG. 5. A function of this relational curve is an exponential function expressed as:

$$\Delta f = \exp(am) \quad (2)$$

where a is the value (or constant) corresponding to the dimension of the turbine blade and m is the amount of time that the turbine blade has been in use. This relational curve shown in FIG. 5 will be referred to hereinafter as a "lifetime predicting curve".

The lifetime predicting curve in FIG. 5 shows that the frequency difference Δf increases exponentially as the amount of time in which the turbine blade has been in use increases to deteriorate the turbine blade progressively. Then, it becomes clear that, if the frequency difference Δf exceeds a predetermined threshold value th on this exponential function, then the turbine blade will suffer from defects, such as cracks or the like.

Accordingly, it is possible to predict the lifetime of a turbine blade by checking the position of the frequency difference Δf on the lifetime predicting curve after the frequency difference Δf is obtained by analyzing the spectrum of the vibration generated when the turbine blade such as one used in a marine gas turbine engine, for example, is made to vibrate by a proper vibrating method, such as an impact method or the like.

To learn the frequency position of the spectrum of the longitudinal waves, as the Equation (1) reveals, it is necessary to obtain the length or distance h between the opposite end faces which are perpendicular to the propagation direction of the longitudinal waves, i.e., the two end faces in the longitudinal direction as a parameter. If the measured object is made to vibrate as described above, then only the longitudinal waves can be extracted. Thus, if velocity c of acoustic waves is known, it is then possible to obtain the value h from the Equation (1) without measuring the dimension of the measured object. The velocity c of acoustic waves can be measured by some suitable conventional methods, such as an ultrasonic wave reflection method in which reflected sounds obtained when the measured object is impacted by ultrasonic waves, for example, are measured.

When a substance is hit at its center of gravity, the vibration of the substance only generates only transverse waves. Therefore, if the frequency of the spectrum of transverse waves is measured by hitting the measured object at its center of gravity, it is then possible to learn the dimension (e.g., diameter d of the cylindrical object 1 shown in FIG. 1A) of the propagation direction of the transverse waves generated from the measured object according to an equation similar to the Equation (1).

Inasmuch as the distance h between the two opposite end faces of the measured object in the longitudinal direction and the dimension of the direction (i.e., transverse wave propagation direction) perpendicular to or crossing the distance h can be known as described above, it is possible to learn the dimension of the measured object only by making the measured object vibrate at its predetermined portion a plurality of times without measuring the size of the measured object in actual practice. If the dimension of the measured object is known, then the value a in the exponential function exp (am) representative of the lifetime predicting curve can be obtained. Therefore, it is possible to learn the amount m of time that the measured object has been in use, i.e., degree of deterioration by the Equation (2) based on the constant a and the frequency difference Δf thus calculated. Thus, how long the measured object will be used safely, i.e., lifetime of the measured object, can be predicted.

A lifetime predicting apparatus for practicing the above-mentioned lifetime predicting method according to one embodiment of the present invention will be described with reference to FIG. 6 and FIGS. 7A, 7B.

Figure 6:
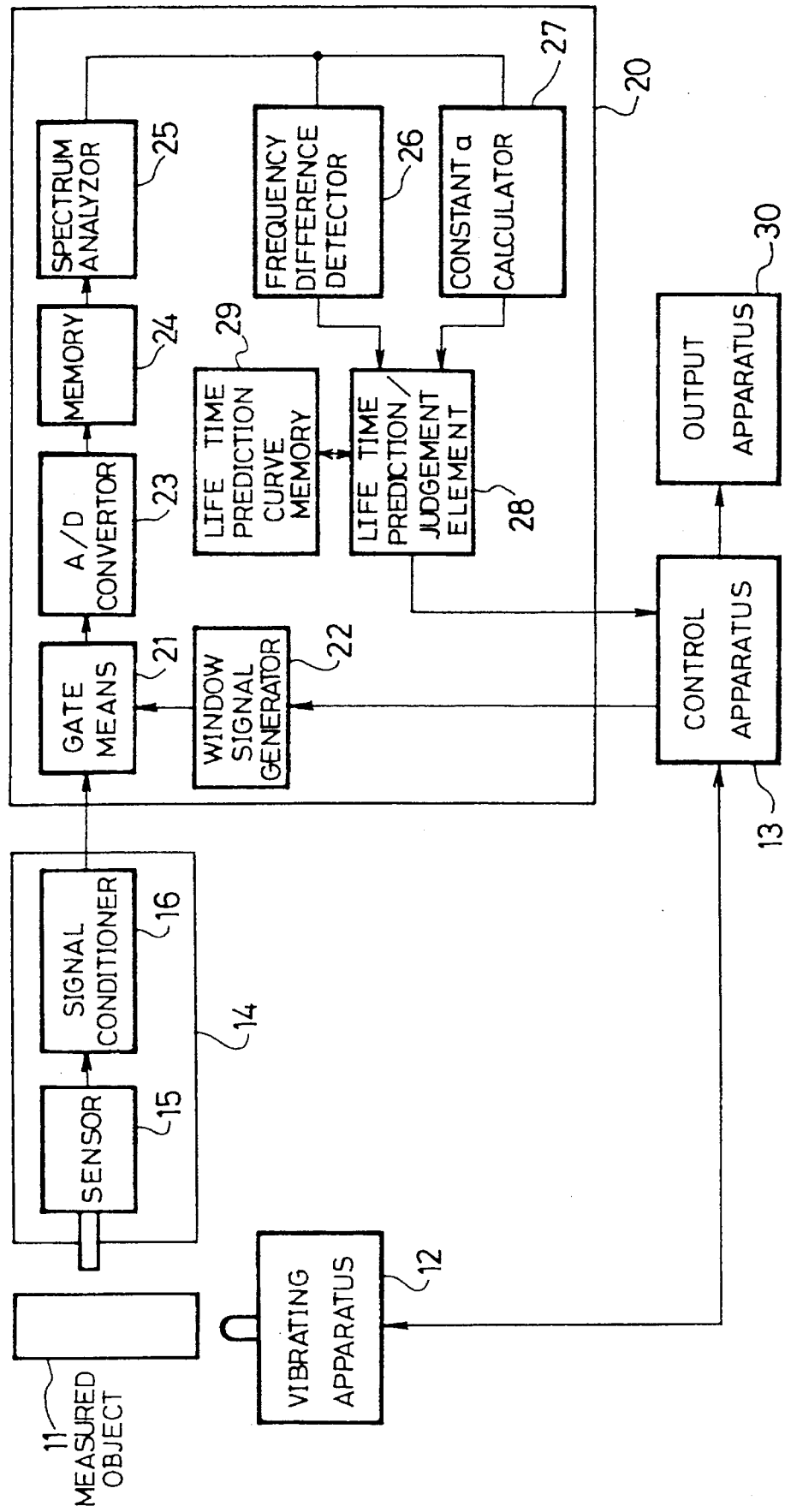
FIG. 6 is a block diagram of a measured object lifetime predicting apparatus according to an embodiment of the present invention.

FIG. 6 is a schematic block diagram showing a lifetime predicting apparatus according to one embodiment of the present invention. In FIG. 6, reference numeral 11 depicts a measured object, 12 a vibrating apparatus, and 13 a control apparatus including a microcomputer (not shown), for example.

The vibrating apparatus 12 makes the measured object 11 to vibrate under the control of the control apparatus 13. In this embodiment, the vibrating apparatus 12 makes the measured object 11 vibrate by a proper impacting device, such as a weight or the like, in a pendulum impact fashion, e.g., so-called impulse impact fashion. A weight driving mechanism of the vibrating apparatus 12 for energizing a weight to impact the measured object 11 is composed of some suitable mechanical elements, such as a cam mechanism or the like (not shown), so that the weight withdraws from the measured object 11 immediately after it impacts the measured object 11. The vibrating apparatus 12 may make the measured object 11 vibrate a plurality of times at its different portions.

In this case, the constant a is not set by entering the values of the length h and the diameter d to the measured object lifetime predicting apparatus as the parameters, after the dimension of the measured object 11 is measured. The vibrating apparatus 12 makes the measured object 11 vibrate in order to calculate the above-mentioned values of the length h and the diameter d from the spectrum of the frequency of oscillation generated.

An output oscillation receiving apparatus 14 receives the oscillations generated when the measured object 11 is made to vibrate by the vibrating apparatus 12. The output oscillations received at the output oscillation receiving apparatus 14 are sensed by a sensor 15 in a non-contacting fashion, and are thereby converted into an electrical signal. The electrical signal from the sensor 15 is processed by a signal processor which is what might be called a signal conditioner 16 in a predetermined signal processing fashion. Any type of sensor 15 may be used as long as it can detect oscillations. For example, a displacement meter, or the like, may by used as the sensor 15. In order to prevent, to the extent possible, the sensor 15 from picking up ambient noise oscillations, the sensor 15 should preferably be a sensor which has a strong directivity in the direction of the measured object 11.

The signal conditioner 16 is formed of a microcomputer which amplifies the electrical signal supplied thereto by the sensor 15 and also removes undesirable high or low band components (i.e., to remove a trend).

The electrical signal from the output oscillation receiving apparatus 14 is supplied to a calculation/judgement apparatus 20. The calculation/judgement apparatus 20 of Fig. 6 includes a microcomputer for example, and performs calculation and judgement, which will be described later on, based on software stored in the microcomputer.

The vibration with which the embodiment of the present invention is concerned is natural vibration inherent in the shape of the measured object. When, however the measured object is forced to vibrate, it is unavoidable that such forced vibration, or the like, is generated together with natural vibration (longitudinal vibration as stationary wave) in the mixed state. Therefore, it is desirable that the vibrations other than the natural vibrations be removed as much as possible. This embodiment meets such a requirement as follows.

Initially, when the measured object 11 is made to vibrate by the vibrating apparatus 12 in order to predict the lifetime of the measured object 11, the measured object 11 is made to vibrate by impacting one of the end faces opposing the longitudinal wave propagation direction, such that the longitudinal wave, which is a compressional wave, becomes superior to or dominates other waves, as described above.

Subsequently, the influence of forced vibration is removed by setting a measurement starting point for measuring the electrical signal by the sensor 15 to a timing point delayed by a predetermined time from the time the measured object 11 is made to vibrate. Specifically, when the measured object 11 is made to vibrate by the vibrating apparatus 12 according to the impulse impact method, vibration starts being measured at a timing point delayed a little from the commencement of vibration of the measured object 11.

The required time period for the measurement to start after the measured object 11 is made to vibrate by the vibrating apparatus 12 is determined as follows. Specifically, the velocity c of acoustic waves propagating through the measured object 11 differs depending upon Young's modulus E (elastic coefficient) and density p of the measured object 11, and has the following relationship expressed as:

$$c_2 = E/p \tag{3}$$

Figure 7A:
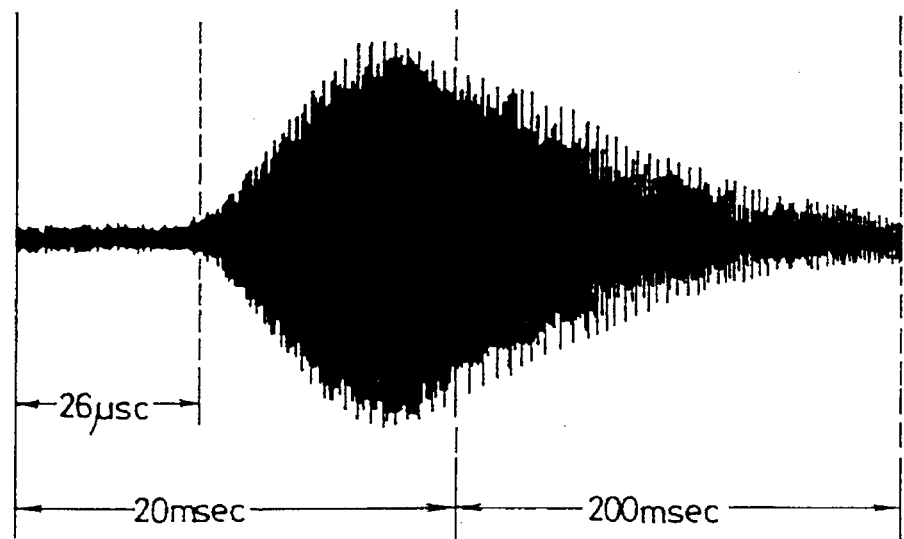
FIGS. 7A and 7B are diagrams that explain the operation of the measured object lifetime measuring apparatus shown in FIG. 6.
Figure 7B:
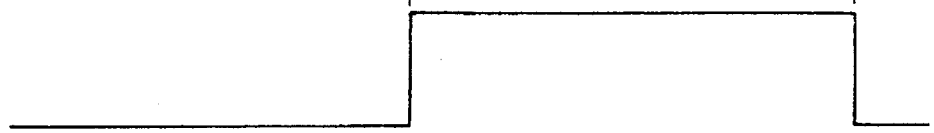

When the measured object 11 is made to vibrate by the impulse impact method according to this embodiment, for example, vibration sensed immediately after the measured object 11 is made to vibrate, has a time series waveform as shown in FIG. 7A. As is clear from FIG. 7A, vibration obtained after the measured object 11 is made to vibrate is similar to seismic waves so that it contains longitudinal waves of high speed and waves of low speed in the mixed state. Also, forced vibration remains. As a consequence, and as shown in FIG. 7A, vibration obtained after the measured object 11 is made to vibrate has no natural vibration waveform peculiar to the shape of the measured object 11. It is considered that the natural vibration wave peculiar to the shape of the measured object 11 can be observed a little before vibration of the intrinsic vibration wave ceases just like an "impression" of a top, for example. For this reason, and according to this embodiment, a window signal or pulse W1 of a square wave shown in FIG. 7B is set, and the vibration wave is extracted based on this window signal W1.

Specifically, the electrical signal input to the calculation/judgement apparatus 20 is supplied to a gate 21 which extracts the natural vibration component peculiar to the shape of the measured object 11 from vibration generated when the measured object 11 is made to vibrate, i.e., impact based on the above window signal W1 supplied thereto from a window signal generator 22. The window signal generator 22 receives vibrating start information from the control apparatus 13 to set a required time period for the window signal W1 to rise following commencement of vibration of the measured object 11 and the width of the window pulse or signal W1. In the example of FIGS. 7A, 7B, the window signal generator 22 causes the window signal W1 to rise at a timing point delayed by twenty milliseconds from a timing point corresponding to commencement of vibration of the measured object 11, and sets a window pulse width of two hundred milliseconds.

In this way, the natural vibration component peculiar to the shape of the measured object 11 is extracted by the window signal W1. The natural vibration component thus extracted by the window signal W1 in the gate 21 is supplied to and converted to digital data by an analog-to-digital (A/D) converter 23 and then written in a memory 24. Then, the digital data written in the memory 24 is read out and supplied to and analyzed by a spectrum analyzer 25.

A constant a calculating means 26 calculates the constant a in the Equation (2) by calculating information concerning the dimension of the measured object 11 from the frequency of the spectrum thus obtained by the spectrum analyzer 25 when the measured object 11 is made to vibrate by the vibrating apparatus 12 in order to calculate information concerning the dimension of the measured object 11.

A frequency difference detector 27 detects the first-order spectrum and a second-order spectrum of the longitudinal waves that is supplied thereto from the spectrum analyzer 25 when the measured object 11 is made to vibrate, in order to predict lifetime of the measured object 11 to thereby calculate the frequency difference $\Delta f$ between the frequencies of the first-order and the second-order spectra.

The lifetime prediction/judgement element 28 is connected with a lifetime prediction curve memory 29. The lifetime prediction curve memory 29 stores a plurality of lifetime prediction curve data using the constant a concerning the dimension of the measured object as a parameter. The data that are stored in the lifetime prediction curve memory 29 contain a threshold value of lifetime which anticipates a safety factor.

The lifetime prediction/judgement element 28 reads out the lifetime prediction curve data of the constant a based on the calculated constant a supplied thereto from the constant a calculator 27 and stores the read-out data in its incorporated buffer memory (not shown).

The lifetime prediction/judgement element 28 determines whether or not the frequency difference $\Delta f$ calculated by the frequency difference detector 26 and the lifetime prediction curve memorized in the buffer memory agree with each other and predicts lifetime of the measured object 11 based on the threshold value th. Then, the lifetime prediction/judgement element 28 supplies the control apparatus 13 with the predicted result, such as information representative of the amount of, or number of times that the measured object 11 can be used and a time period within which the measured object 11 can be used.

The control apparatus 13 supplies the predicted result to an output 30. The output 30 can display the above-mentioned information representing the number of times and the time period on its monitor display (not shown) or can print out the same on a recording paper. Furthermore, the output 30 can let the user know such information by means of sound emanating from a sound generating means (not shown).

While lifetime of the measured object is predicted based on the frequency difference between the frequency of the first-order spectrum and the frequency of the second-order spectrum of the longitudinal waves of the stationary wave vibration generated when the measured object is made to vibrate as described above, the present invention is not limited thereto and the lifetime of the measured object can be predicted based on a difference between frequencies of the second-order spectra or higher-order spectra. Further, the present invention is not limited to longitudinal waves and can employ transverse waves or distortional waves.

A substance generates almost exclusively transverse vibrational waves when made to vibrate at the center of gravity by impact. Therefore, if this vibrating method is employed, it is then possible to predict the lifetime of the substance by extracting only the transverse wave with ease. Further, since the frequency position of the longitudinal wave easily can be determined from the length of the longitudinal direction thereof as described above, it is possible to separate and detect the longitudinal waves from the transverse waves and the distortional waves on the basis of the spectrum position of the longitudinal waves.

Furthermore, it is possible to predict the lifetime of the measured object by inspecting a frequency difference between the frequency of longitudinal wave and the frequency of the distortional wave, similarly, as described above.

As set out, according to the present invention, since the frequency difference $\Delta f$ between the frequency of the nth-order spectrum and the frequency of the (n+1)th-order spectrum of the spectra of the stationary wave vibration generated in the measured object when the measured object is made to vibrate, or the frequency difference $\Delta f$ between the frequency of the longitudinal wave and the frequency of the transverse wave changes in response to degree of deterioration of the measured object, it is possible to predict the lifetime of the measured object by calculating the above frequency difference $\Delta f$.

Furthermore, according to the present invention, since it is possible to predict the lifetime of the measured object by sensing and analyzing in a non-contacting fashion the stationary wave vibration generated in the measured object when the measured object is made to vibrate, it is possible to predict the lifetime of the measured object without damaging the measured object or without deteriorating the measured object, unlike the prior art in which the sensor is brought in contact with the measured object.

Having described a preferred embodiment of the invention with reference to the accompanying drawings, it is to be understood that the invention is not limited to that precise embodiment and that various changes and modifications could be effected therein by one skilled in the art without departing from the spirit or scope of the invention as defined in the appended claims.

What is claimed is:

1. A method of predicting the lifetime of a measured object comprising the steps of:

vibrating a measured object to generate at least one of a group consisting of longitudinal waves, transverse waves, and distortional waves;

detecting a degree of deterioration of said measured object based on a change of frequency difference $\Delta f$ between a frequency of nth-order spectrum and (n+1)th-order spectrum of said at least one of the group; and predicting the lifetime based upon the detected degree of deterioration.

2. A method of predicting the lifetime of a measured object, comprising vibrating a measured object to generate at least a longitudinal wave;

detecting a degree of deterioration of the measured object based on a change of frequency difference $\Delta f$ between a frequency of nth-order spectrum and (n+1)th-order spectrum of at least the longitudinal wave; and predicting the lifetime of the measured object in accordance with said degree of deterioration.

3. A method of predicting the lifetime of a measured object, comprising vibrating a measured object to generate at least longitudinal waves and distortional waves;

detecting a degree of deterioration of said measured object based on the change of a frequency difference $\Delta f$ between a frequency of a spectrum of longitudinal waves and a frequency of a spectrum of distortional waves; and predicting the lifetime of the measured object in accordance with said degree of deterioration.

4. A measured object lifetime predicting apparatus comprising:

vibrating means for making a measured object vibrate;

means for sensing vibration of the measured object and converting said sensed vibration into an electrical signal;

spectrum analyzing means responsive to the electrical signal from said sensing means for analyzing a spectrum of stationary wave vibration of the measured object;

means for detecting a frequency difference $\Delta f$ between a frequency of nth-order spectrum and a frequency of (n+1)th-order spectrum of any one of a group consisting of longitudinal waves, transverse waves and distortional waves;

predicting means for predicting the lifetime of the measured object by detecting a degree of deterioration of the measured object based on a relational curve representing said frequency difference $\Delta f$ and a circumstance of use of the measured object; and output means for outputting a result of said predicting means.

5. A measured object lifetime predicting apparatus comprising:

vibrating means for making a measured object vibrate;

means for sensing the vibration of said measured object and converting the sensed vibration into an electrical signal;

spectrum analyzing means responsive to the electrical signal from said sensing means for analyzing a spectrum of a stationary wave vibration of the measured object;

frequency difference detecting means for detecting a frequency difference $\Delta f$ between a frequency of a spectrum of longitudinal waves and a frequency of a spectrum of distortional waves;

predicting means for predicting the lifetime of said measured object by detecting the degree of deterioration of said measured object based on a relational curve representing said frequency difference $\Delta f$ and a circumstance of use of said measured object; and output means for outputting the prediction.

6. A measured object lifetime predicting apparatus according to claim 4, wherein said predicting means includes a memory for storing information representing the relational curve corresponding to the circumstance of use of the measured object and said detected frequency difference $\Delta f$; and said lifetime of said measured object being predicted from said detected frequency difference $\Delta f$ based on the information stored in said memory.

7. A measured object lifetime predicting apparatus according to claim 5, wherein said predicting means includes a memory for storing information representing the relational curve corresponding to the circumstance of use of the measured object and said detected frequency difference $\Delta f$; and said lifetime of said measured object being predicted from said detected frequency difference $\Delta f$ based on the information stored in said memory.

* * * * *